US008647860B2

(12) United States Patent
Jiang et al.

(10) Patent No.: US 8,647,860 B2
(45) Date of Patent: Feb. 11, 2014

(54) PATHOGEN DETECTION BY SIMULTANEOUS SIZE/FLUORESCENCE MEASUREMENT

(75) Inventors: Jian-Ping Jiang, Tucson, AZ (US); Michael Morrell, Wellington, CO (US); Gregory Scott Morris, Tucson, AZ (US)

(73) Assignee: Azbil BioVigilant, Inc., Tucson, AZ (US)

( * ) Notice: Subject to any disclaimer, the term of this patent is extended or adjusted under 35 U.S.C. 154(b) by 18 days.

(21) Appl. No.: 13/584,685

(22) Filed: Aug. 13, 2012

(65) Prior Publication Data

US 2012/0307234 A1 Dec. 6, 2012

Related U.S. Application Data

(62) Division of application No. 11/768,103, filed on Jun. 25, 2007, now abandoned.

(60) Provisional application No. 60/805,962, filed on Jun. 27, 2006.

(51) Int. Cl.

| | |
|---|---|
| ***C12M 1/34*** | (2006.01) |
| ***C12C 1/15*** | (2006.01) |
| ***C12C 7/06*** | (2006.01) |
| ***C12M 3/00*** | (2006.01) |

(52) U.S. Cl.
USPC .................. 435/288.7; 435/287.1; 435/291.3; 435/291.6; 435/291.7; 435/292.1

(58) Field of Classification Search
None
See application file for complete search history.

(56) References Cited

U.S. PATENT DOCUMENTS

| | | | |
|---|---|---|---|
| 3,497,690 | A | 2/1970 | Wheeless et al. |
| 3,850,525 | A | 11/1974 | Kaye |
| 4,071,298 | A | 1/1978 | Falconer |
| 5,123,731 | A | 6/1992 | Yoshinaga et al. |
| 5,290,707 | A | 3/1994 | Wood |
| 5,292,483 | A | 3/1994 | Kaye |
| 5,540,494 | A | 7/1996 | Purvis, Jr. et al. |
| 5,646,597 | A | 7/1997 | Hamburger et al. |
| 5,701,012 | A | 12/1997 | Ho |
| 5,895,922 | A | 4/1999 | Ho |
| 5,969,622 | A | 10/1999 | Hamburger et al. |

(Continued)

FOREIGN PATENT DOCUMENTS

| | | | |
|---|---|---|---|
| GB | 2420616 | 5/2006 | |
| WO | WO 2005/029046 A2 * | 3/2005 | ............. G01N 15/00 |

(Continued)

OTHER PUBLICATIONS

BioVigilant White Paper, "Instantaneous Microbial Detection" Jan. 2005. p. 1-6. [http://www.biovigilant.com/PDFs/IMD%20for%20Pharmamaceutical%20MFG%2005-05-08.pdf].*

(Continued)

*Primary Examiner* — Ja'na Hines
(74) *Attorney, Agent, or Firm* — Michael J. Curley; Dale F. Regelman; Quarles & Brady LLP

(57) ABSTRACT

A method and apparatus for detecting pathogens and particles in a fluid in which particle size and intrinsic fluorescence of a simple particle is determined.

11 Claims, 3 Drawing Sheets

(56) References Cited

U.S. PATENT DOCUMENTS

| | | | |
|---|---|---|---|
| 5,986,555 | A | 11/1999 | Hamburger et al. |
| 5,999,250 | A | 12/1999 | Hairston et al. |
| 6,008,729 | A | 12/1999 | Hamburger et al. |
| 6,087,947 | A | 7/2000 | Hamburger et al. |
| 6,404,493 | B1 | 6/2002 | Altendorf |
| 6,592,822 | B1 | 7/2003 | Chandler |
| 6,787,104 | B1 | 9/2004 | Mariella, Jr. |
| 6,831,279 | B2 | 12/2004 | Ho |
| 6,885,440 | B2 | 4/2005 | Silcott et al. |
| 7,053,783 | B2 | 5/2006 | Hamburger et al. |
| 7,126,687 | B2 | 10/2006 | Hill et al. |
| 7,430,046 | B2 | 9/2008 | Jiang et al. |
| 7,738,099 | B2 | 6/2010 | Morrell et al. |
| 2002/0045190 | A1 | 4/2002 | Wilson, Jr. et al. |
| 2003/0098422 | A1 | 5/2003 | Silcott et al. |
| 2003/0235919 | A1 | 12/2003 | Chandler |
| 2004/0159799 | A1 | 8/2004 | Saccomanno |
| 2005/0221497 | A1 | 10/2005 | Young |
| 2005/0282219 | A1 | 12/2005 | Prober et al. |
| 2006/0071075 | A1 | 4/2006 | Moon et al. |

FOREIGN PATENT DOCUMENTS

| | | |
|---|---|---|
| WO | WO2005029046 | 3/2005 |
| WO | WO2005033283 | 4/2005 |
| WO | WO2007011854 | 1/2007 |

OTHER PUBLICATIONS

T.H. Jeyes et al., Proc. IRIS Active Systems, vol. 1, p. 235, 1998.

T.V. Inglesby et al., "Anthrax as a Biological Weapon", JAMA, vol. 281, p. 1735, 1999.

Brosseau et al., "Differences in Detected Fluorescence Among Several Bacterial Species Measured with a Direct-Reading Particle Sizer and Fluorescence Detector", Aerosol Science and Technology, 32:545-558, 2000, Taylor and Francis.

Agranovski et al., "Real-time measurement of bacterial aerosols with the UVAPS: performance evaluation", J. Aerosol Sci., 34(3):301-317, 2003, Elsevier.

Kanaani et al., "Performance of UVAPS with respect to detection of airborne fungi", J. Aerosol Sci., 39, pp. 175-189, 2008, Elsevier.

Hairston et al., "Design of an Instrument for Real-Time Detection of Bioaerosols Using Simultaneous Measurement of Particle Aerodynamic Size and Intrinsic Fluorescence," Journal of Aerosol Science, 1997, vol. 28, No. 3, p. 471-482.

Weichert et al., "Determination of Fluorescence Cross-Sections of Biological Aerosols," Particle & Particle Systems Characterization, Jul. 1, 2002, vol. 19, Issue 3, p. 216-222.

"Instantaneous Microbial Detection," BioVigilant White Paper, Jan. 1, 2005, p. 1-6, XP55002158.

"Why Simultaneous Sizing and Fluorescence is Necessary in Order to do Microbial Detection", BioVigilant White Paper, Jan. 1, 2005, XP55002196.

PCT/US2007/072050 International Preliminary Report on Patentability.

PCT/US2008/086886 International Search Report and Written Opinion.

PCT/US2008/083052 International Search Report and Written Opinion.

Office Action received in corresponding Chinese Patent Application No. 200780024666.9.

Chinese Office Action dated Aug. 23, 2011.

Chinese Office Action dated Mar. 23, 2012.

Japanese Patent Office dated Mar. 16, 2012.

EP Supplementary European Search Report.

* cited by examiner

PATHOGEN DETECTION BY SIMULTANEOUS SIZE/FLUORESCENCE MEASUREMENT

CROSS REFERENCE TO RELATED APPLICATION

This application is a divisional of U.S. Non-Provisional Application having Ser. No. 11/768,103, filed on Jun. 25, 2007, now abandoned which in turn claims priority to U.S. provisional application having Ser. No. 60/805,962, filed on Jun. 27, 2006. The contents these applications are incorporated by reference herein in their entirety, for all purposes.

FIELD OF THE INVENTION

The present invention relates generally to a system and method for detecting airborne or waterborne particles, and more particularly to a system and method for detecting airborne or waterborne particles and classifying the detected particles. The invention has particular utility in detecting and classifying allergens and biological warfare agent, and will be described in connection with such utility, although other utilities are contemplated.

BACKGROUND OF THE INVENTION

An urban terrorist attack involving release of biological warfare agents such as bacillus anthracis (anthrax) is presently a realistic concern. Weaponized anthrax spores are extremely dangerous because they can gain passage into the human lungs. A lethal inhalation dose of anthrax spores for humans, LD50 (lethal dose sufficient to kill 50% of the persons exposed) is estimated to be 2,500 to 50,000 spores (see T. V. Inglesby, et al., "anthrax as a Biological Weapon", JAMA, vol. 2801, page 1735, 1999). Some other potential weaponized bio-agents are *yersinia pestis* (plaque), *clostridium botulinum* (botulism), and *francisella tularensis*. In view of this potential threat, there is currently a need for an early warning system to detect such an attack. In the pharmaceutical, healthcare and food industries, a real time detector of environmental microbial level is useful for public health, quality control and regulatory purposes. For example, parental drug manufacturers are required to monitor the microbial levels in their aseptic clean rooms. In these applications, an instrument which can detect microbes in the environment instantaneously will be a useful tool and have advantages over conventional nutrient plate culture methods which requires days for microbes to grow and to be detected.

Particle size measurement and ultraviolet (UV) induced fluorescence detection have been used to detect the presence of biological substances in the air. There exist various patents describing using these techniques as early warning sensors for bio-terrorist attack release of weaponized bio-agents. Among these devices are Biological Agent Warning Sensor (BAWS) developed by MIT Lincoln Laboratory, fluorescence biological particle detection system of Ho (Jim yew-Wah Ho, U.S. Pat. Nos. 5,701,012; 5,895,922; 6,831,279); FLAPS and UV-APS by TSI of Minnesota (Peter P. Hairston; and Frederick R. Quant; U.S. Pat. No. 5,999,250), and a fluorescence sensor by Silcott (U.S. Pat. No. 6,885,440).

A proposed bio-sensor based on laser-induced fluorescence using a pulsed UV laser is described by T. H. Jeys, et al., Proc. IRIS Active Systems, vol. 1, p.235, 1998. This is capable of detecting an aerosol concentration of five particles per liter of air, but involves expensive and delicate instruments. Other particle counters are manufactured by Met One Instrument, Inc, of Grants Pass, Oreg., Particle Measurement Systems, Inc., of Boulder, Colo., and Terra Universal Corp., of Anaheim, Calif.

Various detectors have been designed to detect airborne allergen particles and provide warning to sensitive individuals when the number of particles within an air sample exceeds a predetermined minimum value. These are described in U.S. Pat. Nos. 5,646,597, 5,969,622, 5,986,555, 6,008,729, 6,087,947, and 7,053,783, all to Hamburger et al. These detectors all involve direction of a light beam through a sample of environmental air such that part of the beam will be scattered by any particles in the air, a beam blocking device for transmitting only light scattered in a predetermined angular range corresponding to the predetermined allergen size range, and a detector for detecting the transmitted light.

SUMMARY OF THE INVENTION

For the purpose of detection of microbes in air or water, it is of importance to devise an effective system to measure both particle size and fluorescence generated intrinsically by the microbes. The present invention provides a sensor system which is capable of simultaneously measuring particle size and detecting the presence of intrinsic fluorescence from metabolites and other bio-molecules, on a particle-by-particle basis. The advantages of this detection scheme over the prior art are several. For one it provides a deterministic particle measurement methodology for characterizing particles rather than relying on statistical models employed in prior art for particle characterization. The deterministic measurement methodology enables more definitive assignment of particle characters than the prior art and less reliance on statistical models. It also reduces the possibility of false positives in microbial detection, for example, pollen (larger sizes than microbes) and smoke particles (smaller sizes than microbes) can be excluded from detection. And, it allows detailed analyses of data collected on each individual particle for characterizing the particle, such as intensity of fluorescence signal from a particle as a function of its cross-sectional area or volume, for the purpose of determining the biological status of the particles.

The current invention comprises three main components: (1) a first optical system for measuring an individual particle size; (2) a second optical system to detect a UV laser-induced intrinsic fluorescence signal from an individual particle; and (3) a data recording format for assigning both particle size and fluorescence shy to an individual particle, and computer readable program code for differentiating microbes from non-microbes (e.g. inert dust particles).

The optical assembly of the present invention has two optical sub-assemblies: (a) an optical setup to measure the particle size. As an example, the preferred embodiment of the current invention uses the well-known and often used Mie scattering detection scheme, but applies it in a novel way, enabling the system to make highly accurate measurements of airborne particles with size ranges from 0.5 microns to 20 microns. This capability to make fine distinctions in size is important in order to determine the class of microbe, because different classes of microbes have different size ranges; (b) simultaneous to the particle size measurement, an optical apparatus is used to measure the fluorescence level from the particle being interrogated. As an example, the preferred embodiment of the current invention uses an elliptical minor which is positioned to collected fluorescence emission from the same particle as it is being measured for size.

BRIEF DESCRIPTION OF THE DRAWINGS

Further features and advantages of the present invention will be seen from the following detailed description, taken in conjunction with the accompanying drawings, wherein:

FIG. 2(*b*) is a histogram showing simultaneous measurements of particle size and fluorescence for air containing Baker's yeast powder;

DETAILED DESCRIPTION OF PREFERRED EMBODIMENTS

Figure 4:
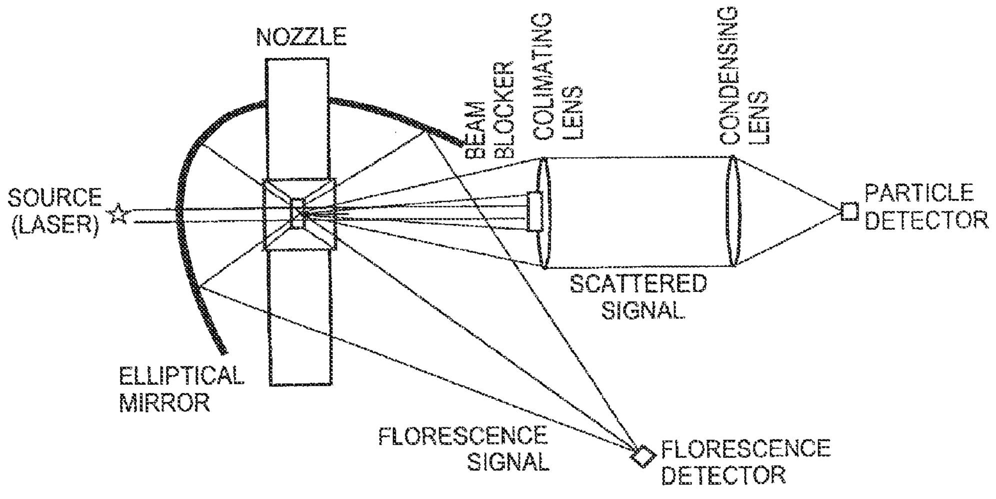
FIG. 4 is a schematic diagram of an optical system accordance with the present invention, for performing simultaneous measurements of particle size and fluorescence.

FIG. 4 is a schematic representation of an optical system for a fluid particle detector system according to a first exemplary embodiment of the invention. This first exemplary embodiment of the system is designed, for example to detect airborne or waterborne bio-terrorist agents deliberately released by terrorists or others, but also may be used in civilian applications to detect harmful levels of other airborne or waterborne particles which may exist naturally such as mold or bacteria, or which may have been accidentally, inadvertently, naturally, or deliberately related, or for other industrial applications such as the food and pharmaceutical manufacturing industries, as well as clean room applications.

The term "fluid borne particles" as used herein means both airborne particles and waterborne particles.

The term "pathogen" as used herein refers to any airborne or waterborne particles, biological agent, or toxin, which could potentially harm or even kill humans exposed to such particles if present in the air or water in sufficient quantities.

The term "biological agent" is defined as any microorganism, pathogen, or infectious substance, toxin, biological toxin, or any naturally occurring, bioengineered or synthesized component of any such microorganism, pathogen, or infectious substance, whatever As origin or method of production. Such biological agents include, for example, biological toxins, bacteria, viruses, rickettsiae, spores, fungi, and protozoa, as well as others known in the art.

"Biological toxins" are poisonous substances produced or derived from plants, animals or microorganisms, but also can be produced or altered by chemical means. A toxin, however, generally develops naturally in a host organism (i.e., saxitoxin is produced by marine algae), but genetically altered and/or synthetically manufactured toxins have been produced in a laboratory environment. Compared with microorganisms, toxins have a relatively simple biochemical composition and are not able to reproduce themselves. In many aspects, they are comparable to chemical agents. Such biological toxins are, for example, botulinum and tetanus toxins, staphylococcal enterotoxin B, tricothocene mycotoxins, ricin, saxitoxin, Shiga and Shiga-like toxins, dendrotoxins, erabutoxin b, as well as other known toxins.

The detector system of the present invention is designed to detect airborne or waterborne particles and produce outputs indicating, for instance, the number of particles of each size within the range, which is detected in a sample, and indicate whether the particles are biologic or non-biologic. The system also may produce an signal or other response if the number of particles exceeds a predetermined value above a normal background level, and/or biological organisms or biological agents and potentially dangerous.

FIG. 4 is a representation of system 10 for a fluid particle detector system according to an exemplary embodiment of the invention. As shown in FIG. 4, the system 10 includes an UV light excitation source 12 such as a laser providing a beam of electromagnetic radiation 14 have an UV light source wavelength. The UV light source is selected to have a wavelength capable of exciting intrinsic fluorescence from metabolites inside microbes. By way of example, the excitation source 12 preferably operates in a wavelength of about 270 nm to about 410 nm, preferably about 350 nm to about 410 nm. A wavelength of about 270 nm to about 410 nm is chosen based on the premise that microbes comprise three primary metabolites: tryptophan, which normally fluoresces at about 270 nm with a range of about 220 nm-about 300 nm; nicotinamide adenine dinucleotide (NADH) which normally fluoresces at about 340 nm (range about 320 nm-about 420 nm); and riboflavin which normally fluoresces at about 400 nm (range about 320 nm-about 420 nm). Preferably, however, the excitation source 12 has a wavelength of about 350 to about 410 nm. This wavelength ensures excitation of two of the three aforesaid primary metabolites, NADH, and riboflavin in bio-agents, but excludes excitation of interferences such as from diesel engine exhaust and other inert particles such as dust or baby powder. Thus, in a preferred embodiment the present invention makes a judicial selection of wavelength range of the excitation source 12, which retains the ability of exciting fluorescence from NADH and riboflavin (foregoing the ability to excite tryptophan) while excluding the excitation of interferents such as diesel engine exhaust. This step is taken to reduce false alarms generated by diesel exhaust (which can be excited by short UV wavelengths such as 266 nm light.

In the system 10 illustrated in FIG. 4, environmental air (or a liquid sample) is drawn into the system through a nozzle 16 for particle sampling. Nozzle 16 has an opening 18 in its middle section to allow the laser beam to pass through the particle stream. Directly downstream front the laser beam is a Mie scattering particle-size detector 20. Mie scattering particle-size detector 20 includes a beam blocker lens 22, a collimator lens 24 and a condenser lens 26 for focusing a portion of the light beam 14 onto a particle detector 28.

Off axis from the laser beam 14, an elliptical mirror 30 is placed at the particle-sampling region in such a way that the intersection of the incoming particle stream and the laser beam is at one of the two foci of the ellipsoid, while a fluorescence detector 32 (in this case a photo-multiplier tube) occupies the other focus. This design utilizes the fact that a point source of light emanating from one of the two foci of an ellipsoid will be focused onto the other. In this optical design, the elliptical mirror 30 concentrates the fluorescence signal from microbe and focus it onto the fluorescence detector 32. An optical filter 34 is placed in front of the fluorescence detector to block the scattered UV light and pass the induced fluorescence.

The beam blocker lens 22 is designed to reflect non-scattered elements of the laser beam 14, and may have a material, such as vinyl, attached a front surface to reflect the non-scattered elements of the beam of electromagnetic radiation. Other features and considerations for the beam blocker lens 22 are disclosed in some of the earlier US patents to Hamburger et al. listed above, and in PCT Application Serial No. PCT/US2006027638, incorporated herein by reference.

The particle detector 20 may comprise, for example, a photodiode for sizing the particles, e.g. as described in the earlier US patent to Hamburger et al., listed above, and incorporated herein by reference The present invention's use of Mie scattering also facilitates the placement of optical components for the detection of UV light illumination to concurrently examine individual particles for the presence of the metabolites NADH, riboflavin and other bio-molecules, which are necessary intermediates for metabolism of living organisms, and therefore exist in microbes such as bacteria and fungi. If these chemical compounds exist in a bio-aerosol, they are excited by the UV photon energy and subsequently emit auto-fluorescence light which may be detected by an instrument based on the detection scheme outlined above. While this detection scheme is not capable of identifying the genus or species of microbes, and viruses may be too small and lack the metabolism for detection, this detection scheme's ability to simultaneously and for each particle determine the size of the particle and if it is biologic or inert indicates to the user the presence Or absence of microbial contamination.

Figure 1:
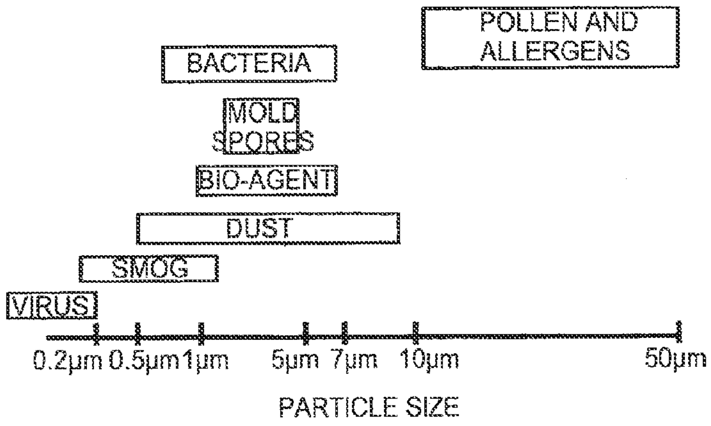
FIG. 1 is a plot showing particle size ranges of several airborne inert and microbial particulates.
Figure 2A:
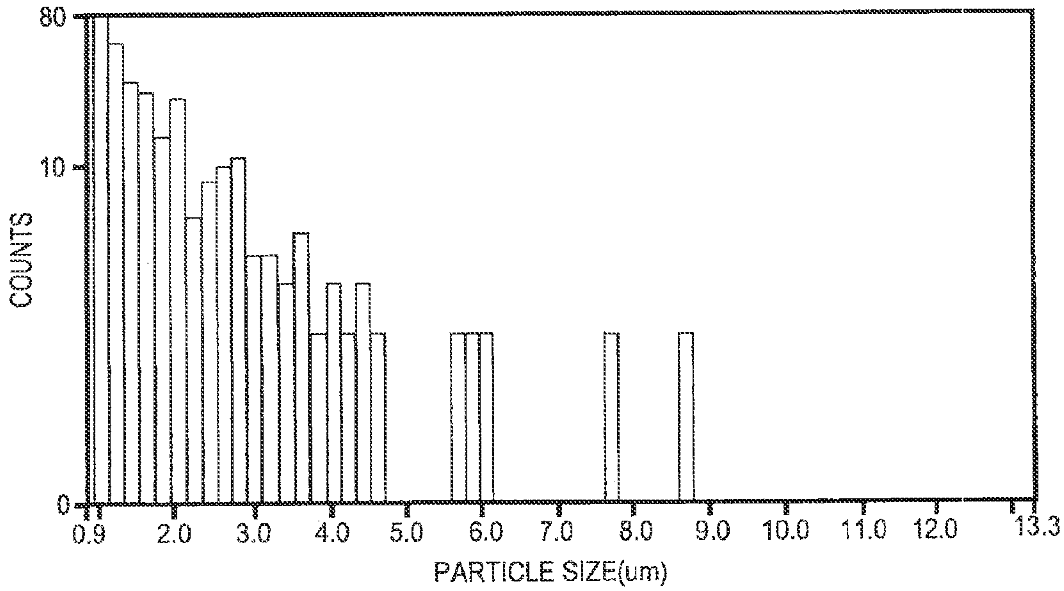
FIG. 2(*a*) is a histogram representation of simultaneous measurements of particle size and fluorescence showing particle distribution for microbe-free air.
Figure 2B:
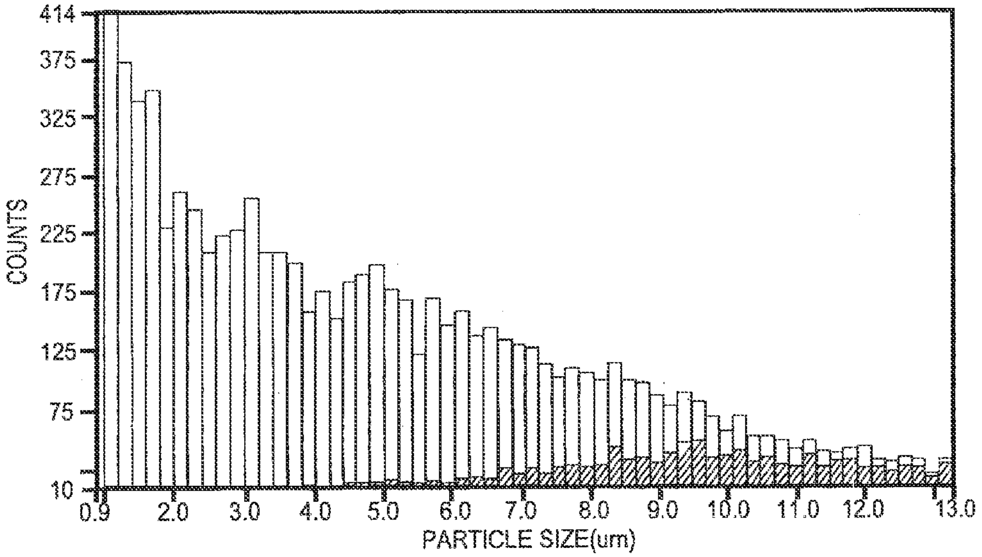
Figure 5:
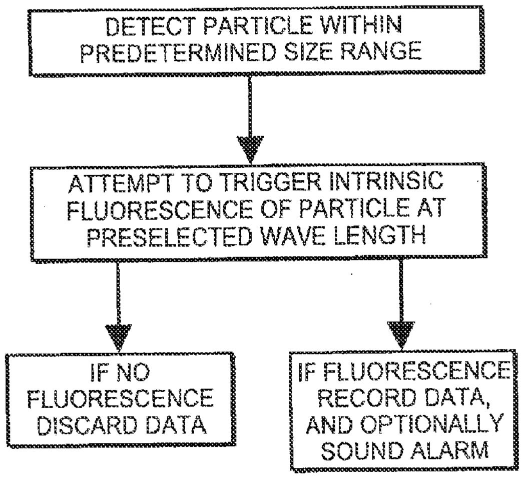
FIG. 5 is a block diagram of the optical system of FIG. 4.

Referring to FIG. 5, the functionality of the simultaneous particle sizing and fluorescence measurement scheme of the present invention is depicted in the graphic presentation of the measurement results from such as an instrument. The principle of operation is as follows: an instrument continuously monitors the environmental air (or liquid) to measure the size of each individual airborne particle in real time and to concurrently determine whether that particle emits fluorescence or not. A threshold is set for the fluorescence signal. If the fluorescence signal is below the set level, the particle is marked inert. This fluorescence signal threshold can be fluorescence signal intensity, fluorescence intensity as a function of particle cross-sectional area or a function of particle volume. If the fluorescence signal threshold exceeds the set level, the particle is marked biological. The combined data of particle size and fluorescence signal strength will determine the presence or absence of microbes on a particle-by-particle basis. FIGS. 2(a) and 2(b) illustrate the functionality of a detector in accordance with the present invention. They show the environmental airborne particle data measured by using this detection scheme. In each graph, the upper part depicts in logarithmic scale the particle size histogram of particle concentration (#/liter of air) versus particle size (from 1 micron to 13 microns); solid bars represent inert particles whereas striped bars indicate the presence of microbes. The lower part of the graph is a real-time snap shot of the particles detected within 1 second: each spike represents one single particle and its height corresponds to the particle size. In FIG. 2(a), the test was done for clean air, so there were only inert particles, free from microbes in a second test, Baker's yeast powder (Saecharernyces cerevisiae) was released into the air. The presence of the microbe was detected and shown by the striped bars in the histogram in FIG. 2(b).

Figure 3:
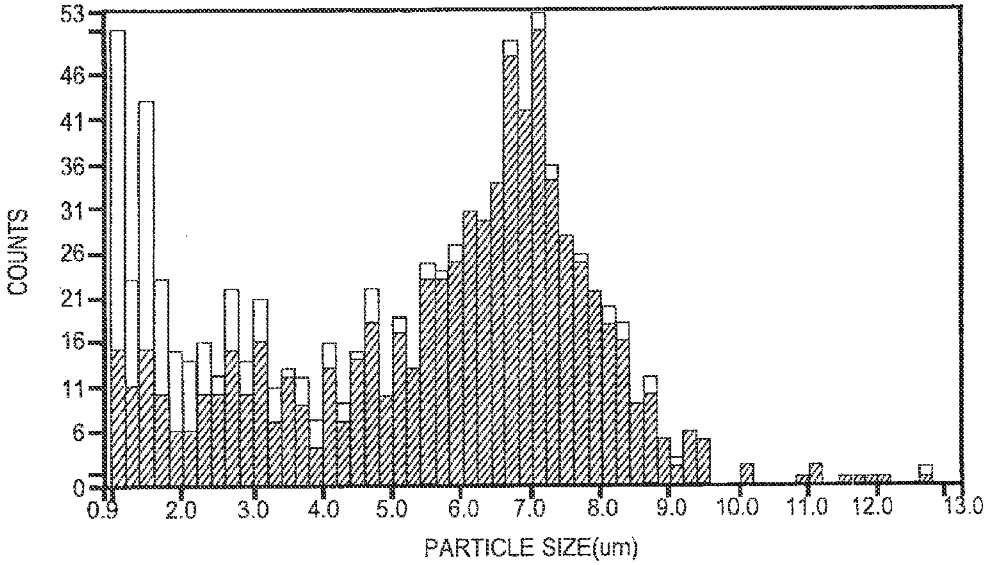
FIG. 3 is a histogram representation of simultaneous measurements of 7 micron size fluorescent dye doped particles and fluorescence.

FIG. 3 shows the data set obtained when 7 microns fluorescent dye doped plastic beads were disseminated into a detector capable of simultaneous particle size and fluorescence measurement scheme. The striped bars show the presence of fluorescence in those particles with a distribution in the 7 microns size range.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiments of the invention without departing substantially from the spirit and principles of the invention. All such modifications and variations are intended to be included herein within the scope of this disclosure and the present invention and, protected by the following claims.

The invention claimed is:

1. A particle detector system, comprising:
a sample cell;
a light source on one side of a sample cell for sending a focused beam of light along a path to and through the sample, the direction of the beam of light through the sample cell defining an axis, whereby portions of the beam of light are scattered at various angles by particles of various sizes present in the sample area, and an unscattered portion of the beam of light remains unscattered;
a beam blocking device on an opposite side of the sample cell along the axis for blocking at least the unscattered portion of the beam of light and configured to limit a range of particles measured, such that light scattered from particles of a predetermined size range proceeds past the beam blocking device along a light path;
a first detector positioned in the light path after the beam blocking device along the axis for detecting a portion of forward scattered light, and producing an output including information on the size of a single particle in the light path within a predetermined size range;
a second detector positioned off the axis from the beam of light for detecting intrinsic fluorescence from said same single particle.

2. The system of claim 1, wherein an elliptical mirror is located in a particle sampling region such that an intersection of the incoming particle stream and the light beam are at one foci of the ellipsoid, and the second detector is at the other foci.

3. The system of claim 1, further comprising an alarm unit for providing a warning signal when a particle within a predetermined size range is detected which also fluoresces.

4. The system of claim 1, wherein the light source emits ultraviolet radiation.

5. The system of claim 1, wherein the light source comprises a LED.

6. The system of claim 5, further comprising a collimator lens optically positioned between the light source and the first detector.

7. The system of claim 1, further comprising a processing unit for processing particle size distribution and particle fluorescence at a give time, and displaying a histogram of the particle on an output device.

8. The system of claim 1, wherein the first detector comprise a photdiode.

9. The system of claim 1, wherein the sample cell comprises an air sample cell.

10. The system of claim 1, wherein the sample cell comprises a water sample cell.

11. The system of claim 1, further comprising computer readable program code for integrating detected particle size and detected intrinsic fluorescence.

* * * * *